United States Patent [19]

Harris

[11] Patent Number: 5,633,327
[45] Date of Patent: May 27, 1997

[54] STYRENE-BASED DICARBOXYLIC ACID-FUNCTIONAL MONOMERS AND POLYMERS PREPARED FROM SAME

[75] Inventor: Rodney M. Harris, Chicago, Ill.

[73] Assignee: The Sherwin-Williams Company, Cleveland, Ohio

[21] Appl. No.: 636,108

[22] Filed: Apr. 22, 1996

Related U.S. Application Data

[62] Division of Ser. No. 424,685, Apr. 18, 1995, Pat. No. 5,510,440, which is a division of Ser. No. 176,606, Jan. 3, 1994, Pat. No. 5,410,078.

[51] Int. Cl.$^6$ .................. C08F 222/02; C08F 8/46; C08F 8/08; C08F 8/14
[52] U.S. Cl. .............. 525/329.6; 525/386; 525/385; 525/384
[58] Field of Search ................ 525/329.6, 384, 525/385, 386

[56] References Cited

U.S. PATENT DOCUMENTS

| | | | |
|---|---|---|---|
| 2,884,408 | 4/1959 | Phillips et al. | 260/78.3 |
| 3,523,143 | 8/1970 | Kwong | 260/835 |
| 3,594,415 | 7/1971 | Zisman et al. | 260/515 |
| 3,803,254 | 4/1974 | Hattori et al. | 260/669 |
| 3,975,314 | 8/1976 | Smyk et al. | 260/2 |
| 4,107,114 | 8/1978 | Nakayama et al. | 260/22 |
| 4,703,101 | 10/1987 | Singer et al. | 528/87 |
| 4,859,758 | 8/1989 | Shalati et al. | 527/313 |
| 4,871,806 | 10/1989 | Shalati et al. | 525/108 |
| 4,927,868 | 5/1990 | Schimmel et al. | 523/439 |
| 5,093,391 | 3/1992 | Barsotti et al. | 523/400 |
| 5,149,737 | 9/1992 | Pontocello et al. | 524/564 |
| 5,210,289 | 5/1993 | Ponticello et al. | 562/426 |
| 5,227,243 | 7/1993 | Shalati et al. | 428/457 |

FOREIGN PATENT DOCUMENTS

0723674  12/1965  Canada .................. 260/479

OTHER PUBLICATIONS

Chemical Abstract 101: 131184q Vinyl citrates from citruc acid as new monomers (Muisers) et al.
Makromol. Chem., Rapid Commun, 8 281–284 (1987) *Copolymerization of 1–hexene–3,4–dioic anhydride and its thermal rearrangement products with styrene.*

Primary Examiner—Joseph L. Schofer
Assistant Examiner—Wu C. Cheng
Attorney, Agent, or Firm—Robert E. McDonald; Steven W. Tan; Heidi A. Boehlefeld

[57] ABSTRACT

An unsaturated acid-functional monomer having the structure:

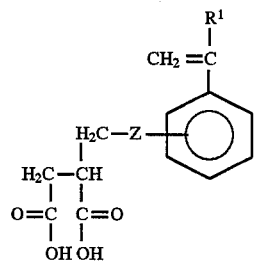

wherein $R^1$ is hydrogen or methyl and Z is nothing or is a divalent radical of 1 to about 20 carbons.

27 Claims, No Drawings

STYRENE-BASED DICARBOXYLIC ACID-FUNCTIONAL MONOMERS AND POLYMERS PREPARED FROM SAME

This is a divisional of applications Ser. No. 08/424,685 filed on Apr. 18, 1995, (now U.S. Pat. No. 5,510,440), which was in turn, a divisional of Ser. No. 08/176,606, filed Jan. 3, 1994 (now U.S. Pat. No. 5,410,078).

BACKGROUND OF THE INVENTION

1. Field of the Invention

This invention involves novel polymerizable monomers having pendent carboxylic acid groups and polymers prepared from those monomers. The monomers have the structure:

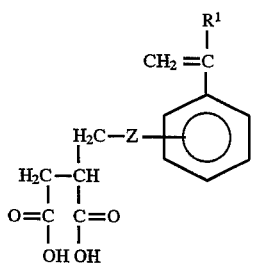

wherein $R^1$ is hydrogen or methyl and Z is nothing or is a divalent alkyl radical of 1 to about 20 carbons. Preferred divalent alkyl radicals are methylene chains —$(-CH_2-)_n$— wherein n is 1 to 20.

This invention also relates to acid-functional polymers obtained by polymerizing, under free radical addition polymerization conditions, (i) the unsaturated acid monomer of this invention; and (ii) optionally, at least one other unsaturated monomer copolymerizable with the unsaturated acid monomer. The acid-functional polymers can be neutralized to provide water-reducible polymers and/or they may be utilized as corrosion or scale inhibitors, thickeners, dispersants and as reactive agents and/or crosslinking agents for compounds having functional groups, such as epoxy, hydroxyl or amine groups, which are reactive with acid groups. The acid-functional polymers can, therefore, be utilized in a variety of materials such as plastics, fibers, adhesives, paper sizing, inks and, particularly, coating compositions.

This invention also relates to novel reactive compositions which utilize the acid-functional polymer in combination with one or more other materials which can react with acid groups. These reactive compositions can be reacted at room temperature or force dried at temperatures ranging up to about 350° F. or higher if desired. When utilized as reactive crosslinking agents for coatings, the acid-functional polymers may be utilized in a variety of coating applications, including primers and topcoats as well as clearcoats and/or basecoats in clearcoat/basecoat compositions.

The reactive compositions typically involve the combination of the acid-functional polymer with an epoxy-functional compound. The reactive composition may, optionally, also incorporate an anhydride-functional compound and, optionally, also a hydroxyl-functional compound. All of these combinations can provide fast reacting, durable coatings which may—minimize the toxicity problems which may be associated with other low temperature curing systems. 2. Description of the Prior Art Unsaturated, polymerizable acids, such as maleic acid, acrylic acid, methacrylic acid and polymers or copolymers incorporating these materials are known in the art. By the selection of one or more of these acids, polymers may be tailored to provide a desired acid value, reactivity or other desired property. The prior art has not, however, taught polymers obtained by the polymerization of the novel styrene-based dicarboxylic acid monomers of this invention.

Coating compositions comprising reactive combinations of epoxy-containing compounds and compounds having acid functionality are known in the art. For example, U.S. Pat. No. 4,859,758 teaches an acid-functional cellulose ester based polymer which could be used in combination with a polyepoxide, and optionally, a polyanhydride and, optionally a hydroxy-functional compound. Similarly, coating compositions comprising cyclic anhydrides and hydroxy-functional compounds are also known in the art. The prior art has not, however, taught the novel acid-functional polymers of this invention nor has it taught coating compositions comprising these acid-functional polymers with epoxy-functional compounds and, optionally, anhydride-functional compounds, and, optionally, hydroxy-functional compounds to provide low temperature curing coatings having excellent durability and performance.

BRIEF SUMMARY OF THE INVENTION

This invention involves unsaturated styrene-based monomers having multiple, pendent acid functionality. The monomers are useful, for example, as neutralizing agents, thickeners, reactive diluents or they can be polymerized to provide acid-functional polymers. These versatile monomers also have a variety of potential applications due to their unique combination of reactive sites. The monomers possess both multiple acid group functionality and also polymerizable unsaturation functionality. Either type of functionality may be reacted first followed, if desired, by subsequent reaction of the other functionality. For example, one or more of the pendent acid groups on the monomer could be reacted with epoxy groups on an epoxide or polyepoxide to provide a hydroxy-functional product having one or more pendent, polymerizable unsaturation sites. Such a product could be subsequently polymerized, either with or without additional copolymerizable monomers such as styrene or (meth)acrylic monomers, by peroxide initiation or by exposure to high energy radiation such as electron beam or ultraviolet light.

A particularly preferred use for the monomers of this invention involves their use in polymers derived by polymerizing the acid monomer through its unsaturation either as a homopolymer or, preferably, in combination with one or more additional copolymerizable monomers. The acid monomers of this invention can be utilized to provide reactivity, water reducibility or other performance property to a copolymer by incorporating these novel monomers into the polymer backbone by free radical polymerization. Furthermore, since the unsaturated acids of this invention are styrene based materials, their reactivity ratios with other polymerizable monomers such as styrene and acrylate or methacrylate monomers under free radical polymerization conditions will be different than the reactivity ratios of the prior art acrylic, methacrylic or maleic acids with those same copolymerizable monomers. Therefore, the monomers of this invention can provide a way to incorporate acid side chains while altering the arrangement of other monomers along the polymeric backbone compared to the use of the common prior art unsaturated acids. Additionally, since the acid groups of the monomer can be, if desired, condensed to form an anhydride group, either before or after polymerization to produce anhydride-functional monomers and/or polymers, the acid monomers of this invention have special utility when utilized as precursors for those anhydride-functional materials.

This invention also elates to curable coating compositions comprising an acid-functional polymer and an epoxy-functional compound, optionally also in combination with other reactive materials such as an anhydride-functional compound. If desired, in addition to the anhydride-functional compound, hydroxy-functional compounds reactive with the anhydrides can be added as well. The term "compound" is used in its broadest sense to include monomers, oligomers and polymers. This invention also relates to substrates coated with the coating compositions of this invention.

In the most preferred coating formulations the epoxy-functional compound is a polyepoxide having an average of at least two epoxy groups, especially cycloaliphatic epoxy groups, per molecule.

Although the curable compositions of this invention can be utilized without solvent in many applications, it is frequently preferred to utilize them in combination with about 5 to about 75% by weight of the total coating composition of an inert solvent. It is convenient to provide the coating composition as a multicomponent system which is reactive upon mixing the components. Especially preferred is a two-component system wherein the acid-functional polymer, and, if utilized, the anhydride-functional compound are combined in one package and the epoxy-functional compound and, if utilized, the hydroxy-functional compound provide a second package. The two packages can then be mixed together to provide the curable coatings immediately prior to application.

In one preferred application, this invention relates to coated substrates having a multi-layer decorative and/or protective coating which comprises:

(a) a basecoat comprising a pigmented film-forming polymer; and (b) a transparent clearcoat comprising a film-forming polymer applied to the surface of the basecoat composition;

wherein the clearcoat and/or the basecoat comprises the curable coating compositions of this invention. The term "film-forming polymer" means any polymeric material which can form a film from evaporation of any carrier or solvent.

Accordingly, one object of this invention is to provide novel unsaturated acid-functional monomers and polymers therefrom. Another object is to provide improved curable compositions having excellent reactivity at low temperatures. It is a further object to provide coating compositions which may be utilized as primers, topcoats or clearcoats and/or basecoats in clearcoat/basecoat compositions. Another object is to provide unsaturated acid-functional monomers which are readily converted to anhydride-functional monomers. Another object is to provide an improved two component coating composition wherein one package comprises an acid-functional polymer and, optionally, an anhydride-functional polymer and the other package comprises an epoxy-functional compound and, optionally, a hydroxy-functional compound. These and other objects will be apparent from the following discussions:

DETAILED DESCRIPTION OF THE INVENTION

1. Dicarboxylic Acid Monomer

The unsaturated styrene based dicarboxylic acid monomers of this invention can be conveniently prepared by the reaction of the anion of a trialkyl-1,1,2-ethanetricarboxylate (such as triethyl-1,1,2-ethanetricarboxylate), with a vinyl benzene alkyl halide (such as vinyl benzyl chloride), followed by hydrolysis of the ester groups to acid groups and subsequent decarboxylation to yield the desired dicarboxylic acid monomer. The vinyl benzene alkyl halide has the general structure:

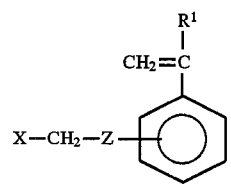

wherein $R^1$ and Z are as defined above and X is a halogen atom. The vinyl benzene alkyl halides of various lengths of Z can be readily prepared by a variety of methods known in the art. For example, Grignard reaction synthesis of the vinyl benzene alkyl halides are representatively set forth in M. L. Hallensleben, *Angew. Makronol. Chem.*, 31, 147 (1973), and Montheard, et al. *J. Polym. Sci. Part A., Polym. Chem.*, 27 (8), 2539 (1989). For cost and availability of starting materials, it is especially preferred that z be nothing or be lower alkyl of 1 to about 4 carbons. Vinyl benzyl chloride, where Z is nothing, $R^1$ is hydrogen, and X is chlorine, is especially preferred.

The reaction to produce the preferred acid-functional monomer is representatively shown below wherein the trialkyl-1,1,2-ethanetricarboxylate is triethyl-1,1,2-ethanetricarboxylate and the vinyl benzene alkyl halide is vinyl benzyl chloride:

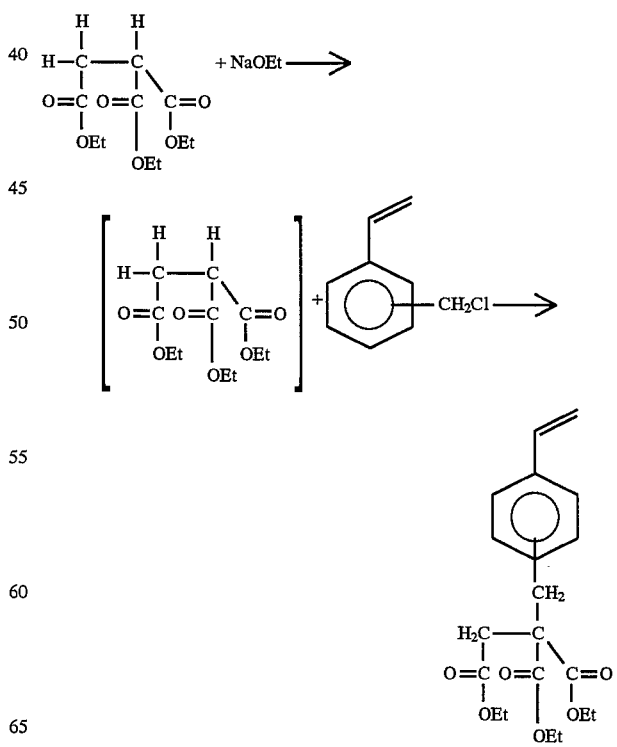

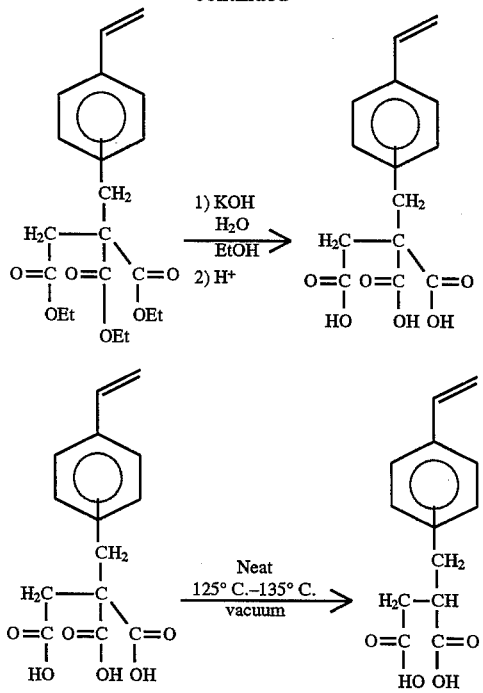

The preparation of the anion of the trialkyl-1,1,2-ethanetricarboxylate is conveniently accomplished by mixing ethanolic sodium ethoxide with the tricarboxylate and refluxing the solution for five to ten minutes. Typically the sodium ethoxide will be present at a level to provide about 0.8 to about 1.1 moles of sodium ethoxide for each mole of tricarboxylate. The anion of the tricarboxylate can then be reacted with the vinyl benzene alkyl halide by mixing the two materials in an approximately 1 to 1 mole ratio and by maintaining the reaction at reflux, in the presence of small amounts (e.g. 500 ppm of the total reaction mixture) of polymerization inhibitors, for 1 to about 3 hours to prepare the vinyl benzene alkyl-1,1,2-ethane tricarboxylate. This tricarboxylate material, in turn, can be hydrolyzed to produce the corresponding tricarboxylic acid by reaction with base, such as sodium hydroxide or potassium hydroxide followed by acidification. Alternatively, the hydrolysis can be conducted by direct reaction of the tricarboxylate with aqueous acid such as aqueous hydrochloric acid. Base hydrolysis is generally preferred and can be readily conducted by admixing an aqueous and/or ethanolic solution of sodium hydroxide or potassium hydroxide and maintaining the reaction mixture at reflux until the reaction is complete (typically 3 to 5 hours). The salt product can be collected by filtration and the tricarboxylic acid is then generated by acidifying an aqueous solution of the salt to a pH less than about 3, typically by using dilute acid such as aqueous hydrochloric acid. The tricarboxylic acid monomer can be converted to tile diacid by heating tile tricarboxylic acid monomer at temperatures over 100° C., typically 115°–140° C., until $CO_2$, evolution ceases. If it is desired to convert tile diacid to the corresponding dicarboxylic acid anhydride, the diacid is then reacted with at least an equimolar amount of a reactant, normally a carboxylic acid derivative such as an anhydride or acid chloride, which will produce a better leaving group than the carboxylic acid —OH. For example, the dicarboxylic acid can be reacted with acetic anhydride followed by subsequent elimination of acetic acid upon ring closure. Acetyl chloride, and especially acetic anhydride, are preferred as the carboxylic acid derivatives. The diacid typically would be admixed with acetic anhydride (typically 1 to 5 moles of acetic anhydride to each mole of diacid) and the solution is heated to 80° C. to 100° C. for approximately 1 to 2 hours to provide the anhydride product. The reaction to produce the anhydride is representatively shown in the schematic below:

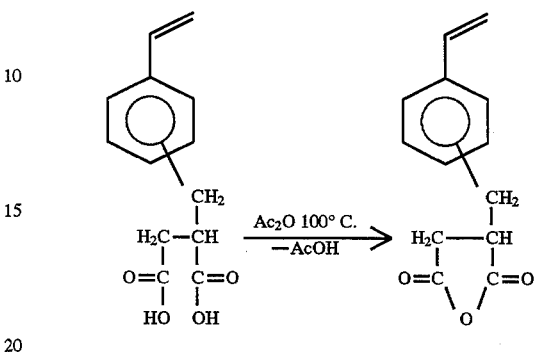

2. Acid-Functional Polymers

The polymerization of the novel monomers of this invention either alone or with other unsaturated copolymerizable monomers, such as (meth)acrylic monomers or styrene, proceeds at excellent yield and can produce polymers having excellent performance characteristics. The monomers are practical for providing any desired acid value for the polymer, which can then, if desired, be neutralized with a base such as ammonia to provide water dispersibility and/or the pendent acid groups can provide reactive sites for other materials having groups reactive with acid groups such as epoxy, amine or hydroxyl groups.

The polymers which incorporate the monomers of this invention could conveniently be prepared by polymerizing the styrene based acid-functional monomer, and, normally, at least one other copolymerizable monomer under free radical addition polymerization conditions. Typically, the polymerization would be conducted in an inert solvent and in the presence of an initiator, such as a peroxide or azo compound, at temperatures ranging from 35° C. to about 120° C., and especially 75° C. to about 100° C. Representative initiators include di-t-butyl peroxide, cumene hydroperoxide, and azobis(isobutyronitrile).

The mixture of monomers used to prepare the polymers would typically comprise from 1 to about 100, and especially 5 to about 30 percent by weight of the styrene based dicarboxylic acid-functional monomer. The remainder of the polymer would be comprised of at least one other unsaturated monomer copolymerizable with the styrene-based acid-functional monomer. One preferred polymer is obtained from a mixture of monomers comprising 5 to about 30 percent by weight of the unsaturated dicarboxylic acid, 10% to about 40% of a copolymerizable hydroxy-functional monomer and 30% to about 85% of at least one other copolymerizable monomer.

Typically, the styrene based acid-functional monomers would be copolymerized with one or more monomers having ethylenic unsaturation and which are not reactive with the acid groups under the conditions of polymerization. Such monomers would include:

(i) acrylic, methacrylic, crotonic, tiglic, or other unsaturated acids or derivatives thereof such as: acrylic acid, methacrylic acid, methyl acrylate, ethyl acrylate, propyl acrylate, isopropyl acrylate, butyl acrylate, isobutyl acrylate, ethylhexyl acrylate, amyl acrylate, 3,5,5- trimethylhexyl acrylate, methyl methacrylate, ethyl methacrylate, propyl methacrylate, dimethylaminoethyl methacrylate, isobornyl methacrylate, t-butyl methacrylate, ethyl tiglate, methyl crotonate, ethyl crotonate, 2-hydroxyethyl acrylate, 2-hydroxyethylmethacrylate, 2-hydroxypropyl acrylate, 4-hydroxybutyl methacrylate, 2-hydroxypropyl methacrylate, 3-hydroxybutyl acrylate, 4-hydroxybutyl acrylate, 4-hydroxypentyl acrylate, 2-hydroxyethyl ethacrylate, 3-hydroxybutyl methacrylate, 2-hydroxyethyl chloroacrylate, diethylene glycol methacrylate, tetra ethylene glycol acrylate, etc.;

(ii) vinyl compounds such as vinyl acetate, vinyl propionate, vinyl butyrate, vinyl isobutyrate, vinyl benzoate, vinyl m-chlorobenzoate, vinyl p-methoxybenzoate, vinyl α-chloroacetate, vinyl toluene, vinyl chloride, para vinyl benzyl alcohol, etc.;

(iii) styrene-based materials such as styrene, α-methyl styrene, α-ethyl styrene, α-bromo styrene, 2,6-dichlorostyrene, etc.;

(iv) allyl compounds such as allyl chloride, allyl acetate, allyl benzoate, allyl methacrylate, etc.;

(v) other copolymerizable unsaturated monomers such as ethylene, acrylonitrile, methacrylonitrile, dimethyl maleate, isopropenyl acetate, isopropenyl isobutyrate, acrylamide, methacrylamide, and dienes such as 1,3-butadiene, etc.

The free radical addition polymers of this invention could typically be used as lacquers or as reactive polymers and would have application in adhesives, coatings, inks, plastics, chemical additives and fibers. The pendent acid functionality makes them especially useful as water reducible polymers.

3. Reaction Coating Compositions

If the acid-functional polymer contains other reactive functionality in addition to acid functionality, such as hydroxyl groups, it could also be used with crosslinkers reactive with hydroxyl groups such as a polyisocyanate, or a nitrogen resin such as a condensate of an aldehyde such as formaldehyde with a nitrogenous compound such as urea, melamine or benzoguanamine or a lower alkyl ether of such a condensate.

The novel acid-functional polymers of this invention could also be combined with compounds which are reactive with acid functionality to produce reactive coating compositions. These reactive coating compositions could comprise:

(i) the acid-functional polymer and a polyepoxide;

(ii) the acid-functional polymer, a polyanhydride and a monoepoxide or polyepoxide; or (iii) the acid-functional polymer, a polyanhydride, a mono- or polyepoxide, and a hydroxy-functional compound.

3.A. Epoxy-Functional Compounds

The preferred reactive compositions of this invention typically require the use of at least one epoxy-functional compound. The epoxy compound, preferably, will be a polyepoxide having an average of at least two epoxy groups per molecule. If the acid-functional polymer of this invention is used in combination with an anhydride-functional compound and, optionally a hydroxy-functional compound, then either a monoepoxide or a polyepoxide can be used.

Representative useful monoepoxides include the monoglycidyl ethers of aliphatic or aromatic alcohols such as butyl glycidyl ether, octyl glycidyl ether, nonyl glycidyl ether, decyl glycidyl ether, dodecyl glycidyl ether, p-tert-butylphenyl glycidyl ether, and o-cresyl glycidyl ether. Monoepoxy esters such as the glycidyl ester of versatic acid (commercially available as CARDURA® E from Shell Chemical Company), or the glycidyl esters of other acids such as tertiary-nonanoic acid, tertiary-decanoic acid, tertiary-undecanoic acid, etc. are also useful. Similarly, if desired, unsaturated monoepoxy esters such as glycidyl acrylate, glycidyl methacrylate or glycidyl laurate could be used. Additionally, epoxidized oils having an average of one epoxy group per molecule could also be used as monoepoxides.

Other useful monoepoxies include styrene oxide, cyclohexene oxide, 1,2-butene oxide, 2,3-butene oxide, 1,2-pentene oxide, 1,2-heptene oxide, 1,2-octene oxide, 1,2-nonene oxide, 1,2-decene oxide, and the like.

It is only necessary that the monoepoxide compounds have a sufficiently low volatility to remain in the coating composition under the applicable conditions of cure.

Polyepoxides are especially preferred in the reactive coatings of this invention. Especially preferred as the polyfunctional epoxy compounds, due to their reactivity and durability, are the polyepoxy-functional cycloaliphatic epoxies. Preferably, the cycloaliphatic epoxies will have a number average molecular weight less than about 2,000 to minimize the viscosity. The cycloaliphatic epoxies are conveniently prepared by methods well known in the art such as epoxidation of dienes or polyenes, or the epoxidation of unsaturated esters by reaction with a peracid such as peracetic and/or performic acid.

Commercial examples of representative preferred cycloaliphatic epoxies include 3,4-epoxycyclohexylmethyl 3,4-epoxy cyclohexane carboxylate (e.g. "ERL-4221" from Union Carbide Corp.); bis(3,4-epoxycyclohexylmethyl) adipate (e.g. "ERL-4299" from Union Carbide Corporation); 3,4-epoxy-6-methylcyclohexylmethyl 3,4-epoxy-6-methylcyclohexane carboxylate (e.g. "ERL-4201" from Union Carbide Corp.); bis(3,4-epoxy-6-methylcyclohexylmethyl)adipate (e.g. "ERL-4289" from Union Carbide Corp.); bis(2,3-epoxycyclopentyl) ether (e.g. "ERL-0400" from Union Carbide Corp.); dipentene dioxide (e.g. "ERL-4269" from Union Carbide Corp.); 2-(3,4-epoxycyclohexyl-5,5-spiro-3-4-epoxy) cyclohexane-metadioxane (e.g. "ERL-4234" from Union Carbide Corp.). Other commercially available cycloaliphatic epoxies are available from Ciba-Geigy Corporation such as CY 192, a cycloaliphatic diglycidyl ester epoxy resin having an epoxy equivalent weight of about 154. The manufacture of representative epoxies is taught in various patents including U.S. Pat. Nos. 2,750,395; 2,884,408; 2,890,194; 3,027,357 and 3,318,822.

Other polyepoxides potentially useful in the practices of this invention include aliphatic and aromatic polyepoxies, such as those prepared by the reaction of an aliphatic polyol or polyhydric phenol and an epihalohydrin. Other useful epoxies include epoxidized oils and epoxy-functional copolymers such as acrylic polymers derived from ethylenically unsaturated epoxy-functional monomers such as glycidyl acrylate or glycidyl methacrylate in combination with other copolymerizable monomers such as the (meth)acrylic and other unsaturated monomers. Representative useful (meth)acrylic monomers include methyl acrylate, ethyl acrylate, propyl acrylate, isopropyl acrylate, butyl acrylate, isobutyl acrylate, ethyl hexyl acrylate, amyl acrylate, 3,5,5-trimethylhexyl acrylate, methyl methacrylate, lauryl methacrylate, butyl methacrylate, 2-hydroxyethyl methacrylate, acrylonitrile, methacrylonitrile, acrylamide and methacrylamide. Other copolymerizable monomers include vinyl acetate, vinyl propionate, vinyl butyrate, vinyl isobutyrate, vinyl benzoate, vinyl m-chlorobenzoate, vinyl p-methoxy benzoate, vinyl chloride, styrene, α-methyl styrene, diethyl fumarate, dimethyl maleate, etc. Monomers having acid functionality, or other functionality reactive with epoxide groups should normally not be utilized in the manufacture of the polyepoxide vehicle.

The ratio of acid groups to epoxy groups can be widely varied to give any desired level of crosslinking within the practice of this invention. When the reactive coating system comprises just the acid-functional polymer and a polyepoxide, at least 0.1 acid groups should be present for each epoxy group. It is generally preferred, however, to provide about 0.1 to about 2.0 acid groups for each epoxy group in such a reactive system, and especially preferred to provide about 0.3 to about 1.0 acid groups for each epoxy group in such a system.

It is especially preferred in the practice of this invention to include a catalyst for the reaction of epoxy and acid groups. Tertiary amines, secondary amines such as ethyl imidazole, quaternary ammonium salts, and nucleophilic catalysts such as lithium iodide, phosphonium salts, and phosphines such as triphenyl phosphine are especially useful as catalysts for epoxy/acid reactions. The catalyst for the epoxy/acid reaction will typically be present at a level of at least 0.01% by weight of the total acid-functional polymer and epoxy-functional compound and will preferably be present at about 0.1 to about 3.0%.

3.B. Anhydride Functional Compounds

Useful reactive coating compositions incorporating the acid-functional polymer of this invention and an epoxy-functional compound may, optionally, also incorporate an anhydride-functional compound to alter various performance properties of the final coating. The anhydride-functional compounds which are useful in the practice of this invention can be any aliphatic or aromatic compound having at least two cyclic carboxylic acid anhydride groups in the molecule. Polymeric anhydrides having number average molecular weights between 500 and 7,000 are most useful. Especially preferred in the practice of this invention is the use of acrylic polymers having anhydride functionality. These are conveniently prepared as is well known in the art by the polymerization under free radical addition polymerization conditions of at least one unsaturated monomer having anhydride functionality, such as maleic anhydride, citraconic anhydride, itaconic anhydride, propenyl succinic anhydride, etc. optionally with other ethylenically unsaturated monomers such as the esters of unsaturated acids, vinyl compounds, styrene-based materials, allyl compounds and other copolymerizable monomers, all as representatively taught elsewhere in this specification.

The monomers which are copolymerized with the unsaturated anhydride monomer should, of course, be free of any functionality which could react with the anhydride group during the polymerization. These anhydride-functional polymers can be conveniently prepared by conventional free radical addition polymerization techniques. Typically the polymerization will be conducted in an inert solvent and in the presence of an initiator at temperatures ranging from 35° C. to about 200° C. The anhydride-functional free radical addition polymers should typically comprise at least 5% by weight of the anhydride. An especially preferred anhydride-functional polymer comprises the free radical addition polymerization product of (a) 5 to 40, and especially 15 to about 25, weight percent of an ethylenically unsaturated monoanhydride and (b) 60 to 95, and especially 75 to about 85, weight percent of at least one other ethylenically unsaturated monomer copolymerizable with the ethylenically unsaturated anhydride.

Other polyanhydrides can also be optionally utilized in the practice of this invention. Ester anhydrides can be prepared, as is known in the art, by the reaction of e.g. trimellitic anhydride with polyols. Other representative, suitable polyanhydrides include poly-functional cyclic dianhydrides such as cyclopentane tetracarboxylic acid dianhydride, diphenyl-ether tetracarboxylic acid dianhydride, 1,2,3,4,-butane tetracarboxylic acid dianhydride, and the benzophenone tetracarboxylic dianhydrides such as 3,3',4,4'-benzophenone tetracarboxylic dianhydride, and 2,bromo-3,3',4,4'-benzophenone tetracarboxylic acid dianhydride. Trianhydrides such as the benzene and cyclohexene hexacarboxylic acid trianhydrides are also useful. Additionally, useful polyanhydrides can be prepared by the maleinization of polyunsaturated compounds such as unsaturated rubbers, unsaturated oils and unsaturated hydrocarbons.

Although it is not our intent to be bound by theory, it is believed that in the course of the curing reaction of the components of this invention, that at least some of the acid groups and epoxy groups react to produce ester groups and hydroxyl groups and that at least some of these hydroxyl groups are reacted with the anhydride groups to produce ester groups and additional acid groups. It is, therefore, especially preferred in the practice of this invention to include a catalyst for the reaction of anhydride groups and hydroxyl groups and also a catalyst for the reaction of epoxy and acid groups.

When the reactive coating composition incorporates a polyanhydride-functional compound along with the acid-functional polymer and the epoxy-functional compound, the ratios of anhydride to acid to epoxy groups can be widely varied to give any desired level of crosslinking within the practice of this invention. Typically, the polyanhydride should be present in an amount to provide at least about 0.01 anhydride groups for each epoxy group in the reactive coating. It is preferred, however, to provide about 0.3 to about 6.0 acid groups and about 0.6 to about 12.0 epoxy groups for each anhydride group in the reactive system. An especially preferred formulation range provides 2.0 to about 5.0 acid groups and 3.0 to about 8.0 epoxy groups for each anhydride group.

3.C. Hydroxy-Functional Compounds

If desired, the reactive coating compositions of this invention which comprise the acid-functional polymer, the epoxy-functional compound and the anhydride-functional compound can also incorporate a hydroxy-functional compound. The hydroxy-functional compounds which are useful in the practice of this invention have an average of at least two hydroxyl groups per molecule. Although low molecular weight diols and polyols such as propylene glycol, 1,6-hexanediol, triethanol amine, and pentaerythritol can be utilized in the practice of this invention, it is especially preferred to utilize polymeric hydroxy-functional compounds such as polyethers, polyesters, acrylics, polyurethanes, polycaprolactones, etc.

Preferably the hydroxy-functional polymer will have a number average molecular weight of at least about 400. Typical number average molecular weights will range from about 400 to about 30,000, and especially 1,000 to about 15,000. In order to provide the fastest rate of reaction during cure it is preferred in the practice of this invention to utilize hydroxy-functional compounds having predominantly, and preferably all, primary hydroxyl functionality.

Representative hydroxy-functional polymers include those described in Sections 3.C. 1 through 3.C.5 below:

3.C.1.

Polyether polyols are well known in the art and are conveniently prepared by the reaction of a diol or polyol with the corresponding alkylene oxide. These materials are commercially available and may be prepared by a known process such as, for example, the processes described in *Encyclopedia of Chemical Technology*, Volume 7, pages 257–262, published by Interscience Publishers, Inc., 1951; and in Kirk-Othmer *Encyclopedia of Chemical Technology*, Volume 18, pages 638–641, published by Wiley-International, 1982. Representative examples include the polypropylene ether glycols and polyethylene ether glycols such as those marketed as Niax® Polyols from Union Carbide Corporation.

3.C.2.

Another useful class of hydroxy-functional polymers are those prepared by condensation polymerization reaction techniques as are well known in the art. Representative condensation polymerization reactions include polyesters prepared by the condensation of polyhydric alcohols and polycarboxylic acids or anhydrides, with or without the inclusion of drying oil, semi-drying oil, or non-drying oil fatty acids. By adjusting the stoichiometry of the alcohols and the acids while maintaining an excess of hydroxyl groups, hydroxy-functional polyesters can be readily produced to provide a wide range of desired molecular weights and performance characteristics.

The polyester polyols are derived from one or more aromatic and/or aliphatic polycarboxylic acids, the anhydrides thereof, and one or more aliphatic and/or aromatic polyols. The carboxylic acids include the saturated and unsaturated polycarboxylic acids and the derivatives thereof, such as maleic acid, fumaric acid, succinic acid, adipic acid, azelaic acid. and dicyclopentadiene dicarboxylic acid. The carboxylic acids also include the aromatic polycarboxylic acids, such as phthalic acid, isophthalic acid, terephthalic acid, etc. Anhydrides such as maleic anhydride, phthalic anhydride, trimellitic anhydride, or Nadic Methyl Anhydride (brand name for methylbicyclo[2.2.1]heptene-2,3-dicarboxylic anhydride isomers) can also be used.

Representative saturated and unsaturated polyols which can be reacted with the carboxylic acids to produce hydroxy-functional polyesters include diols such as ethylene glycol, dipropylene glycol, 2,2,4-trimethyl 1,3-pentanediol, neopentyl glycol, 1,2-propanediol, 1,4-butanediol, 1,3-butanediol, 2,3-butanediol, 1,5-pentanediol, 1,6-hexanediol, 2,2-dimethyl-1,3-propanediol, 1,4-cyclohexanedimethanol, 1,2-cyclohexanedimethanol, 1,3-cyclohexanedimethanol, 1,4-bis(2-hydroxyethoxy)cyclohexane, trimethylene glycol, tetramethylene glycol, pentamethylene glycol, hexamethylene glycol, decamethylene glycol, diethylene glycol, triethylene glycol, tetraethylene glycol, norbornylene glycol, 1,4-benzenedimethanol, 1,4-behzenediethanol, 2,4-dimethyl-2-ethylenehexane-1,3-diol, 2-butene- 1,4-diol, and polyols such as trimethylolethane, trimethylolpropane, trimethylolhexane, triethylolpropane, 1,2,4-butanetriol, glycerol, pentaerythritol, dipentaerythritol, etc.

Typically, the reaction between the polyols and the polycarboxylic acids is conducted at about 120° C. to about 200° C. in the presence of an esterification catalyst such as dibutyl tin oxide.

3.C.3.

Additionally, hydroxy-functional polymers can be prepared by the ring opening reaction of epoxides and/or polyepoxides with primary or, preferably, secondary amines or polyamines to produce hydroxy-functional polymers. Representative amines and polyamines include ethanol amine, N-methylethanol amine, dimethyl amine, ethylene diamine, isophorone diamine, etc. Representative polyepoxides include those prepared by condensing a polyhydric alcohol or polyhydric phenol with an epihalohydrin, such as epichlorohydrin, usually under alkaline conditions. Some of these condensation products are available commercially under the designations EPON or DRH from Shell Chemical Company, and methods of preparation are representatively taught in U.S. Pat. Nos. 2,592,560; 2,582,985 and 2,694,694.

3.C.4.

Other useful hydroxy-functional polymers can be prepared by the reaction of at least one polyol, such as those representatively described in Section 3.C.2 above, with polyisocyanates to produce hydroxy-functional urethanes. Representative polyisocyanates having two or more isocyanate groups per molecule include the aliphatic compounds such as ethylene, trimethylene, tetramethylene, pentamethylene, hexamethylene, 1,2-propylene, 1,2-butylene, 2,3-butylene, 1,3-butylene, ethylidene and butylidene diisocyanates; the cycloalkylene compounds such as 3-isocyanatomethyl-3,5,5-trimethylcyclohexylisocyanate, and the 1,3-cyclopentane, 1,3-cyclohexane, and 1,2-cyclohexane diisocyanates; the aromatic compounds such as m-phenylene, p-phenylene, 4,4'-diphenyl, 1,5-naphthalene and 1,4-naphthalene diisocyanates; the aliphatic-aromatic compounds such as 4,4'-diphenylene methane, 2,4- or 2,6-toluene, or mixtures thereof, 4,4'-toluidine, and 1,4-xylylene diisocyanates; the nuclear substituted aromatic compounds such as dianisidine diisocyanate, 4,4'-diphenylether diisocyanate and chlorodiphenylene diisocyanate; the triisocyanates such as triphenyl methane-4,4',4"-triisocyanate, 1,3,5-triisocyanate benzene and 2,4,6-triisocyanate toluene; and the tetraisocyanates such as 4,4'-diphenyl-dimethyl methane-2,2'-5,5'-tetraisocyanate; the polymerized polyisocyanates such as tolylene diisocyanate dimers and trimers, and other various polyisocyanates containing biuret, urethane, and/or allophanate linkages. The polyisocyanates and the polyols are typically reacted at temperatures of 25° C. to about 150° C. to form the hydroxy-functional polymers.

3.C.5.

Useful hydroxy-functional polymers can also be conveniently prepared by free radical polymerization techniques such as in the production of acrylic resins. The polymers are typically prepared by the addition polymerization of one or more monomers. At least one of the monomers will contain, or can be reacted to produce, a reactive hydroxyl group. Representative hydroxy-functional monomers include 2-hydroxyethyl acrylate, 2-hydroxypropyl acrylate, 4-hydroxybutyl methacrylate, 2-hydroxypropyl methacrylate, 3-hydroxybutyl acrylate, 4-hydroxybutyl acrylate, 4-hydroxypentyl acrylate, 2-hydroxyethyl ethacrylate, 3-hydroxybutyl methacrylate, 2-hydroxyethyl chloroacrylate, diethylene glycol methacrylate, tetraethylene glycol acetate, para-vinyl benzyl alcohol, etc. Typically the hydroxy-functional monomers would be copolymerized with one or more monomers having ethylenic unsaturation such as the non-hydroxy-functional monomers included in Section 2 above.

The acrylics are conveniently prepared by conventional free radical addition polymerization techniques. Frequently, the polymerization will be catalyzed by conventional initiators known in the art to generate a free radical such as azobis(isobutyronitrile), cumene hydroperoxide, t-butyl perbenzoate, etc. Typically, the unsaturated monomers are heated in the presence of the free radical initiator at temperatures ranging from about 35° C. to about 200° C., and especially 100° C. to 160° C., to effect the polymerization. The molecular weight of the polymer can be controlled, if desired, by the monomer selection, reaction temperature and time, and/or the use of chain transfer agents as is well known in the art.

Especially preferred in the practice of this invention are hydroxy-functional polyesters and hydroxy-functional acrylic polymers. An especially preferred hydroxy-functional polymer is the addition polymerization reaction product of (a) 10 to about 40 weight percent of a hydroxy-functional ethylenically unsaturated monomer and (b) 60 to about 90 weight percent of at least one ethylenically unsaturated monomer copolymerizable with the hydroxy-functional monomer.

When the reactive coating system incorporates a hydroxy-functional compound along with the acid-functional polymer, the epoxy-functional compound, and polyanhydride compound, the relative levels of each of these reactive groups may also be widely varied within the practice of this invention. It is preferred, however, to provide about 0.05 to about 3.0 acid groups and about 0.5 to about 4.0 epoxy groups and about 0.5 to about 6.0 hydroxyl groups for each anhydride group in the reactive system. An especially preferred formulation range provides 1.0 to about 2.0 acid groups and 1.0 to about 3.0 epoxy groups and about 1.0 to about 4.0 hydroxyl groups for each anhydride group.

It is especially preferred in the practice of this invention when using anhydride-functional compounds in combination with the acid-functional polymers and epoxy-functional compounds to include a catalyst for the reaction of the epoxy and acid groups and a catalyst for the reaction of anhydride groups and hydroxyl groups as taught in this specification. It is especially preferred in the practice of this invention to utilize tertiary amines and especially N-methylimidazol as a catalyst for the anhydride/hydroxyl reaction. The catalyst for the anhydride/hydroxyl reaction will typically be present at a level of at least 0.01% by weight of the anhydride compound and preferably 1.0 to about 5.0%.

If desired, more than one of any of the acid-functional, anhydride-functional, epoxy-functional or hydroxy-functional compounds could be utilized in a single curable coating formulation.

The coatings of this invention can be cured at temperatures ranging from about room temperature up to about 350° F. The coatings can be used as clear coatings and/or they may contain pigments as is well known in the art. Representative opacifying pigments include white pigments such as titanium dioxide, zinc oxide, antimony oxide, etc. and organic or inorganic chromatic pigments such as iron oxide, carbon black, phthalocyanine blue, etc. The coatings may also contain extender pigments such as calcium carbonate, clay, silica, talc, etc.

The coatings may also contain other additives such as flow agents, catalysts, diluents, solvents, ultraviolet light absorbers, etc.

Since the curable compositions of this invention are typically provided a multi-package systems which must be mixed together prior to use, the pigments, catalysts and other additives can be conveniently added to any or all of the appropriate individual packages.

The coatings of this invention may typically be applied to any substrate such metal, plastic, wood, glass, synthetic fibers, etc. by brushing, dipping, roll coating, flow coating, spraying or other method conventionally employed in the coating industry.

One preferred application of the curable coatings of this invention relates to their use as clearcoats and/or basecoats in clearcoat/basecoat formulations.

Clearcoat/basecoat systems are well known, especially in the automobile industry where it is especially useful to apply a pigmented basecoat, which may contain metallic pigments, to a substrate and allow it to form a polymer film followed by the application of a clearcoat which will not mix with or have any appreciable solvent attack upon the previously applied basecoat. The basecoat composition may be any of the polymers known to be useful in coating compositions including the reactive compositions of this invention.

One useful polymer basecoat includes the acrylic addition polymers, particularly polymers or copolymers of one or more alkyl esters of acrylic acid or methacrylic acid, optionally together with one or more other ethylenically unsaturated monomers. These polymers may be of either the thermoplastic type or the thermosetting, crosslinking type which contain hydroxyl or amine or other reactive functionality which can be crosslinked. Suitable acrylic esters and unsaturated monomers for either type of polymer include methyl methacrylate, ethyl methacrylate, propyl methacrylate, butyl methacrylate, ethyl acrylate, butyl acrylate, vinyl acetate, acrylonitrile, acrylamide, styrene, vinyl chloride, etc. Where the polymers are required to be of the crosslinking type, suitable functional monomers which can be used in addition to those already mentioned include acrylic or methacrylic acid, hydroxy ethyl acrylate, 2-hydroxy propyl methacrylate, glycidyl acrylate, tertiary-butyl amino ethyl methacrylate, etc. The basecoat composition may, in such a case, also contain a crosslinking agent such as a carbodiimide, a polyanhydride, a polyisocyanate, a polyepoxide, or a nitrogen resin such as a condensate of an aldehyde such as formaldehyde with a nitrogenous compound such as urea, melamine or benzoguanamine or a lower alkyl ether of such a condensate. Other polymers useful in the basecoat composition include vinyl copolymers such as copolymers of vinyl esters of inorganic or organic acids, such as vinyl chloride, vinyl acetate, vinyl propionate, etc., which copolymers may optionally be partially hydrolyzed so as to introduce vinyl alcohol units.

Other polymers useful in the manufacture of the basecoat include alkyd resins or polyesters which can be prepared in a known manner by the condensation of polyhydric alcohols and polycarboxylic acids, with or without the inclusion of natural drying oil fatty acids as described elsewhere in this specification. The polyesters or alkyds may contain a proportion of free hydroxyl and/or carboxyl groups which are available for reaction, if desired with suitable crosslinking agents as discussed above.

If desired, the basecoat composition may also contain waxes, rheology modifiers, cellulose esters, or other additives to alter the appearance, drying or viscosity characteristics of the basecoat.

Typically, the basecoat will include pigments conventionally used for coating compositions and after being applied to a substrate, which may or may not previously have been primed, the basecoat will be allowed sufficient time to form a polymer film which will not be lifted during the application of the clearcoat. The basecoat may be heated or merely allowed to air-dry to form the film. Generally, the basecoat will be allowed to dry for about 1 to 20 minutes before application of the clearcoat. The clearcoat is then applied to the surface of the basecoat, and the system can be allowed to dry at room temperature or, if desired, can be force dried by baking the coated substrate at temperatures typically ranging up to about 350° F.

Typically, the clearcoat may contain ultraviolet light absorbers or stabilizers, such as hindered phenols or hindered amines at a level ranging up to about 6% by weight of the vehicle solids as is well known in the art. The clearcoat can be applied by any application method known in the art, but preferably will be spray applied. If desired, multiple layers of basecoat and/or clearcoat can be applied. Typically, both the basecoat and the clearcoat will each be applied to give a dry film thickness of about 0.01 to about 6, and especially about 0.5 to about 3.0 mils.

If desired, the novel reactive compositions taught herein could be used as a basecoat, in which case the clearcoat could also comprise the novel reactive coatings taught herein, or other polymers, including the polymers taught herein as being useful as basecoat formulations could be utilized as clearcoats.

The following examples have been selected to illustrate specific embodiments and practices of advantage to a more complete understanding of the invention. Unless otherwise stated, "parts" means parts-by-weight and "percent" is percent-by-weight.

The starting raw materials utilized in these examples are commercially available. The vinyl benzyl chloride is a 70/30 meta/para isomer commercially available from Dow Chemical Company. The sodium metal, diethyl malonate, ethyl chloroacetate, acetic anhydride, butylated hydroxy toluene, and the triethyl-1,1,2-ethanetricarboxylate, were obtained from Aldrich Chemical Company. The absolute ethanol was obtained from USI-Quantum Chemical Company.

EXAMPLE A

Triethyl 1-(¾ vinyl benzyl)-1,1,2-ethane tricarboxylate

A sodium ethoxide/ethanol solution was prepared by slowly adding 16.02 g of sodium metal to 365 g of absolute ethanol with slow stirring. The mixture was then heated at reflux for 5–10 minutes. Triethyl- 1,1,2-ethane tricarboxylate ( 180 g from Aldrich Chemical Company) was added over 20 minutes to the mixture at room temperature. The mixture was heated at reflux for 5–10 minutes, then cooled to 25° C. Next, 112.9 g of vinyl benzyl chloride was added over 20 minutes (maximum temperature of the reaction mixture was 45° C.). A small amount of butylated hydroxy toluene inhibitor was added. The mixture was heated to reflux for 2 hours, then cooled to room temperature.

The reaction mixture was neutralized (pH ~7) with glacial acetic acid. About two-thirds of the ethanol was stripped off under reduced pressure. Six hundred sixty-five milliliters of deionized water was added and the product was extracted with toluene. The combined toluene extracts were dried over sodium sulfate. Removing the volatiles with rotary evaporation produced 255.2 g of triethyl-1-(¾-vinyl benzyl)-1,1,2-ethane tricarboxylate as a yellow liquid in an isolated yield of 96% of theory. NMR and infrared spectral data confirmed the structure of the tricarboxylate product.

EXAMPLE B 1-(¾-Vinyl benzyl)-1,1,2-ethane tricarboxylic acid

An aqueous/ethanolic potassium hydroxide solution was prepared by slowly mixing 2805 ml of absolute ethanol and 147.5 ml of deionized water. A small amount of butylated hydroxy toluene inhibitor was added. Potassium hydroxide (363 g) was added slowly keeping the temperature below reflux. The mixture was then cooled to 30° C. and 240 g, (approximately 0.662 mol) of the crude product of the vinyl benzyl triester of Example A was quickly added. The mixture rapidly turned cloudy and then became homogeneous upon heating to reflux. An additional small amount of butylated hydroxy toluene inhibitor was again added and reflux was continued for 4 hours. The precipitate laden mixture was then allowed to cool to room temperature. The tricarboxylate salt was collected by suction filtration, then dissolved in deionized water (800 ml) and neutralized with dilute aqueous hydrochloric acid (5:1 conc. HCl/H$_2$O vol, ratio) to a Ph<2. Two additions of approximately 3000 ml each of anhydrous acetone was added to the acidified solution and the potassium chloride precipitate was filtered off. The acetone was then stripped off and the process was then repeated. The remaining volatiles were then removed under reduced pressure to give an isolated yield of 113.1 g (74.4%) of an off white solid (mp 112.5°–125° C. decomposed). NMR, infrared and acid dissociation constants data were used to characterize the tricarboxylic acid product. In water, aqueous potassium hydroxide titration identified the Pka's of the three carboxylic acid groups as 2.60; 4.59 and 8.06.

EXAMPLE C 2-(¾-Vinyl benzyl) Succinic Acid

A flask containing 5.0 g (0.018 mol) of the vinyl benzyl ethane triadic of Example B and a small amount of butylated hydroxy toluene inhibitor was evacuated and filled with nitrogen three times. Then the material was heated to 120°–135° C. Gas evolution began on melting and continued briskly for about 2.5 hours. The reaction mixture viscosity increased with some gas evolution over 2.5 hours, after which the product was cooled to room temperature. Acetone (10 times reaction mixture volume) was added and the mixture stirred. Insoluble polymer was filtered off and the volatiles were then stripped away under reduced pressure to give 3.49 g of a brown, viscous, oily diacid (82.9% isolated yield) which did not crystallize. NMR and infrared spectral data confirmed the structure of the product as the desired 2-(¾ vinyl benzyl) succinic acid.

EXAMPLE D

Hydroxy-Functional Copolymer

A representative hydroxy-functional polymer incorporating the styrene based acid-functional monomer of this invention could be prepared, in a representative fashion, as follows:

A reaction vessel equipped with a mechanical stirrer, water cooled condenser, nitrogen inlet, water trap, thermometer and heating mantel could be charged with 172.5 parts of n-butyl acetate and heated to approximately 200° and a monomer premix comprising 91.2 parts of methyl methacrylate, 58 parts of butyl acrylate, 58 parts of hydroxy ethyl methacrylate, 25 parts of the monomer of Example C, 54 parts styrene and an initiator premixture composed of 11.5 parts of n-butyl acetate and 5.7 parts of 2,2'-azobis(2-methylbutyronitrile) could be metered simultaneously into the polymerization reactor at a constant rate for approximately 4 hours. The reaction temperature could be maintained for an additional 2 hours after the addition was completed and then allowed to cool to yield the hydroxy-functional acrylic polymer incorporating the styrene based dicarboxylic acid of this invention. Such a hydroxy-functional polymer could be neutralized with a base such as ammonia to provide water dispersibility and could be utilized in an aqueous coating composition in combination with a typical crosslinking agent, such as a melamine curing agent or a blocked isocyanate to provide curable, water reducible coating compositions.

EXAMPLE E

Acid-Functional Polymer

An acid-functional polymer could be prepared, in a representative fashion, as follows:

A reaction vessel equipped as described in Example D could be charged with 170.0 parts of n-butyl acetate and heated to approximately 200° F. and a monomer premix comprising, representatively, 80.0 parts methyl methacrylate, 60 parts butyl acrylate, 95 parts of the monomer of Example C, 50 parts styrene and an initiator premixture composed of 11.0 parts; of n-butyl acetate and 6.0 parts of 2,2'-azobis(2-methylbutyronitrile) could be metered simultaneously into the polymerization reactor at a constant rate for several hours. The reaction temperature would be maintained for several hours after the addition was completed to yield the acrylic polymer incorporating the dicarboxylic acid of this invention. Such an acid-functional polymer could be utilized in combination with a polyepoxide, such as ERL-4299 to produce a curable composition.

Another potential utility for the acid-functional monomers of this invention is as precursors for the production of dicarboxylic anhydride monomers. These anhydride monomers have special utility due to their low temperature reactivity with hydroxyl groups and their convenient polymerization through their unsaturation to produce anhydride-functional polymers. Representative production of such an anhydride monomer is shown in Example F.

EXAMPLE F 2-(¾-Vinyl benzyl) Succinic Anhydride

A mixture of 3.49 g (0.0149 mol) of the vinyl benzyl succinic acid of Example C, 4.04 g (3.73 ml, 0.0396 mol) of acetic anhydride and a small amount of butylated hydroxy toluene inhibitor was prepared. The reaction mixture was stirred and heated to 100° C. A temperature of 100°–103° C. was maintained for 1.5 hours. After cooling the reaction mixture to room temperature, acetone (10 times the reaction mixture volume) was added. Insoluble polymer was removed by filtration. Volatiles were then stripped from the filtrate leaving 3.11 g (96.6% isolated yield) of a brown viscous oil which was identified by NMR and infrared spectral data as the desired 2-(¾ vinyl benzyl) succinic anhydride.

While this invention has been described by a specific number of embodiments, other variations and modifications may be made without departing from the spirit and scope of the invention as set forth in the appended claims.

The entire disclosure of all applications, patents and publications cited herein are hereby incorporated by reference.

The invention claimed is:

1. A curable composition comprising:
   (i) an acid-functional polymer comprising the free radical addition polymerization product of a mixture of monomers comprising:
      (a) 5% to 30% by weight of an unsaturated acid-functional monomer having the structure:

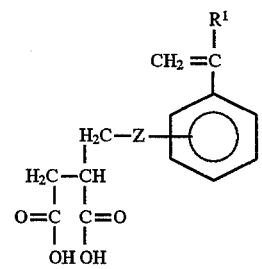

wherein $R^1$ is hydrogen or methyl and Z is nothing or is a divalent radical of 1 to about 20 carbons; and
      (b) 10% to about 40% by weight of a copolymerizable hydroxy-functional monomer; and
      (c) 30% to about 85% by weight of at least one other copolymerizable monomer
   (ii) a crosslinker reactive with hydroxyl groups.

2. A curable composition which comprises:
   (i) an acid-functional polymer comprising the free radical addition polymerization product of a mixture of monomers comprising:
      (a) 1% to 100% by weight of an unsaturated acid-functional monomer having the structure:

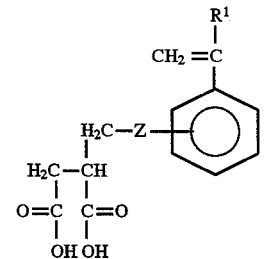

wherein $R^1$ is hydrogen or methyl and Z is nothing or is a divalent radical of 1 to about 20 carbons; and
      (b) 0% to 99% by weight of at least one other unsaturated monomer copolymerizable with the unsaturated acid-functional monomer; and
   (ii) a compound having an average of at least two functional groups per molecule which are reactive with acid groups.

3. The curable composition of claim 2 wherein the acid-functional polymer is the reaction product of 5 to about 30 weight percent of the unsaturated acid-functional monomer and 70 to about 95 weight percent of at least one other unsaturated monomer copolymerizable with the unsaturated acid-functional monomer.

4. The curable composition of claim 2 wherein the compound having an average of at least two functional groups per molecule reactive with acid groups is a polyepoxide.

5. The curable composition of claim 4 wherein the polyepoxide is a cycloaliphatic polyepoxide.

6. The curable composition of claim 4 wherein the polyepoxide is a polymer obtained by the polymerization of an ethylenically unsaturated epoxy-functional monomer and at least one other copolymerizable ethylenically unsaturated monomer.

7. The curable composition of claim 2 wherein Z is nothing.

8. The curable composition of claim 2 wherein Z is a divalent polymethylene chain —(—CH$_2$—)$_n$— wherein n is 1 to 20.

9. A curable composition which comprises:
(i) an acid-functional polymer comprising the free radical addition polymerization product of a mixture of monomers comprising:
(a) 1% to 100% by weight of an unsaturated acid-functional monomer having the structure:

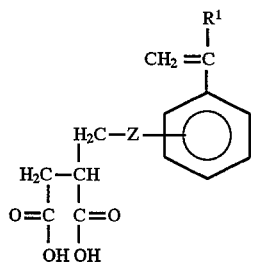

wherein R$^1$ is hydrogen or methyl and Z is nothing or is a divalent radical of 1 to about 20 carbons; and
(b) 0% to 99% by weight of at least one other unsaturated monomer copolymerizable with the unsaturated acid-functional monomer; and
(ii) an epoxy-functional compound; and
(iii) an anhydride-functional compound having an average of at least two anhydride groups per molecule.

10. The curable composition of claim 9 wherein the acid-functional polymer is the reaction product of 5 to about 30 weight percent of the unsaturated acid-functional monomer and 70 to about 95 weight percent of at least one other unsaturated monomer copolymerizable with the unsaturated acid-functional monomer.

11. The curable composition of claim 9 wherein the epoxy-functional compound is monoepoxide.

12. The curable composition of claim 9 wherein the epoxy-functional compound is a polyepoxide having an average of at least two epoxy groups per molecule.

13. The curable composition of claim 12 wherein the polyepoxide is a cycloaliphatic polyepoxide.

14. The curable composition of claim 12 wherein the polyepoxide is a copolymer obtained by the copolymerization of an ethylenically unsaturated epoxy-functional monomer and at least one other copolymerizable ethylenically unsaturated monomer.

15. The curable composition of claim 9 wherein the anhydride-functional compound and the acid-functional polymer and the epoxy-functional compound are each present at a level to provide 0.3 to about 6.0 acid groups and 0.6 to 12.0 epoxy groups for each anhydride group.

16. The curable composition of claim 9 wherein the composition also comprises a catalyst for the reaction of acid groups and epoxy groups and a catalyst for the reaction of anhydride groups and hydroxyl groups.

17. A curable composition which comprises:
(i) an acid-functional polymer comprising the free radical addition polymerization product of a mixture of monomers comprising:
(a) 1% to 100% by weight of an unsaturated acid-functional monomer having the structure:

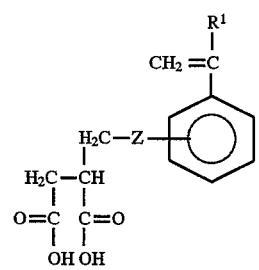

wherein R$_1$ is hydrogen or methyl and Z is nothing or is a divalent radical of 1 to about 20 carbons; and
(b) 0% to 99% by weight of at least one other unsaturated monomer copolymerizable with the unsaturated acid-functional monomer; and
(ii) an epoxy-functional compound; and
(iii) an anhydride-functional compound having an average of at least two anhydride groups per-molecule; and
(iv) a hydroxy-functional compound having an average of at least two hydroxyl groups per molecule.

18. The curable composition of claim 17 wherein the acid-functional polymer is the reaction product of 5 to about 30 weight percent of the unsaturated acid-functional monomer and 70 to about 95 weight percent of at least one other unsaturated monomer copolymerizable with the unsaturated acid-functional monomer.

19. The curable composition of claim 17 wherein the epoxy-functional compound is a monoepoxide.

20. The curable composition of claim 17 wherein the epoxy-functional compound is a polyepoxide having an average of at least two epoxy groups per molecule.

21. The curable composition of claim 20 wherein the polyepoxide is a cycloaliphatic polyepoxide.

22. The curable composition of claim 20 wherein the polyepoxide is a copolymer obtained by the copolymerization of an ethylenically unsaturated epoxy-functional monomer and at least one other copolymerizable ethylenically unsaturated monomer.

23. The curable composition of claim 17 wherein the anhydride-functional compound, the acid-functional polymer, the epoxy-functional compound and the hydroxy-functional compound are each present at a level to provide 0.5 to about 3.0 acid groups and 0.5 to about 4.0 epoxy groups and about 0.5 to about 6.0 hydroxyl groups for each anhydride group.

24. The curable composition of claim 17 wherein the composition also comprises a catalyst for the reaction of acid groups and epoxy groups and a catalyst for the reaction of anhydride groups and hydroxyl groups.

25. The curable composition of claim 17 wherein the hydroxy-functional compound (iv) is a hydroxy-functional polymer having a number average molecular weight of at least 400.

26. The curable composition of claim 17 wherein Z is nothing.

27. The curable composition of claim 17 wherein Z is a divalent polymethylene chain —(—CH$_2$—)— wherein n is 1 to 20.

* * * * *